US008936377B2

(12) United States Patent
Papac et al.

(10) Patent No.: US 8,936,377 B2
(45) Date of Patent: Jan. 20, 2015

(54) APPARATUS FOR ENHANCING BRIGHTNESS OF A WAVELENGTH CONVERTING ELEMENT

(75) Inventors: Michael James Papac, Tustin, CA (US); Christopher Horvath, Lake Forest, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 714 days.

(21) Appl. No.: 12/751,127

(22) Filed: Mar. 31, 2010

(65) Prior Publication Data
US 2011/0245820 A1 Oct. 6, 2011

(51) Int. Cl.
| | | |
|---|---|---|
| F21V 13/12 | (2006.01) | |
| F21V 8/00 | (2006.01) | |
| A61B 1/06 | (2006.01) | |
| A61B 3/00 | (2006.01) | |
| F21K 99/00 | (2010.01) | |
| H01L 33/50 | (2010.01) | |
| G02F 1/35 | (2006.01) | |

(52) U.S. Cl.
CPC .......... *A61B 3/0008* (2013.01); *G02B 6/0006* (2013.01); *A61B 1/0653* (2013.01); *F21K 9/56* (2013.01); *A61B 1/0669* (2013.01); *H01L 33/505* (2013.01); *G02F 1/353* (2013.01); *G02B 6/0003* (2013.01); *H01L 33/507* (2013.01)
USPC .................. 362/231; 362/84; 606/4; 606/10; 606/11

(58) Field of Classification Search
CPC .......................... F21L 19/00; F21W 2131/406
USPC ............. 606/1–6; 607/88–94; 362/2, 84, 166, 362/293
See application file for complete search history.

(56) References Cited

U.S. PATENT DOCUMENTS

| | | | |
|---|---|---|---|
| 3,796,886 A * | 3/1974 | Freeman .................... | 250/493.1 |
| 5,099,399 A | 3/1992 | Miller et al. | |
| 5,465,170 A | 11/1995 | Arimoto | |
| 5,526,190 A | 6/1996 | Hubble et al. | |
| 6,268,613 B1 | 7/2001 | Cantu et al. | |
| 6,272,269 B1 | 8/2001 | Naum | |

(Continued)

FOREIGN PATENT DOCUMENTS

| | | |
|---|---|---|
| JP | 2006518939 A1 | 8/2006 |
| JP | 2009043668 A | 2/2009 |

OTHER PUBLICATIONS

International Search Report for PCT/US2011/027,936, 2 pages.
(Continued)

*Primary Examiner* — William Thomson
*Assistant Examiner* — Jeffrey Lipitz
(74) *Attorney, Agent, or Firm* — Jason Finch

(57) ABSTRACT

Disclosed is an exemplary illumination device for enhancing the brightness of wavelength converting element. The illumination device includes a wavelength converting element operable for receiving light from a light source at a first wavelength range and converting the light to a second wavelength range. The wavelength converting element includes a first face, a second face opposite the first face, and a side edge extending between the first and second faces. A reflective optical element is arranged adjacent the side edge of the wave converting element. The reflective optical element is configured to reflect light in at least the first wavelength range toward the wavelength converting element.

21 Claims, 7 Drawing Sheets

(56) References Cited

U.S. PATENT DOCUMENTS

| | | | |
|---|---|---|---|
| 6,332,688 B1* | 12/2001 | Magarill | 359/858 |
| 6,459,844 B1 | 10/2002 | Pan | |
| 6,510,995 B2 | 1/2003 | Muthu et al. | |
| 6,540,670 B1 | 4/2003 | Hirata et al. | |
| 6,730,940 B1 | 5/2004 | Steranka et al. | |
| 6,850,673 B2 | 2/2005 | Johnston, II et al. | |
| 7,070,300 B2* | 7/2006 | Harbers et al. | 362/231 |
| 7,217,022 B2 | 5/2007 | Ruffin | |
| 7,245,072 B2 | 7/2007 | Ouderkirk et al. | |
| 7,276,737 B2 | 10/2007 | Camras et al. | |
| 7,349,163 B2 | 3/2008 | Angelini et al. | |
| 7,403,680 B2 | 7/2008 | Simbal | |
| 7,672,041 B2 | 3/2010 | Ito | |
| 7,682,027 B2 | 3/2010 | Buczek et al. | |
| 7,918,583 B2 | 4/2011 | Chakmakjian et al. | |
| 2002/0003928 A1 | 1/2002 | Bischel et al. | |
| 2003/0112421 A1 | 6/2003 | Smith | |
| 2003/0147254 A1 | 8/2003 | Yoneda et al. | |
| 2003/0230751 A1* | 12/2003 | Harada | 257/80 |
| 2004/0145913 A1 | 7/2004 | Ouderkirk et al. | |
| 2005/0174779 A1 | 8/2005 | Yoneda et al. | |
| 2005/0270775 A1 | 12/2005 | Harbers et al. | |
| 2006/0018125 A1 | 1/2006 | Miller et al. | |
| 2006/0044820 A1 | 3/2006 | Ruffin | |
| 2006/0203468 A1 | 9/2006 | Beeson et al. | |
| 2007/0081336 A1* | 4/2007 | Bierhuizen et al. | 362/293 |
| 2007/0133211 A1 | 6/2007 | Yoneda et al. | |
| 2007/0284597 A1 | 12/2007 | Nawashiro et al. | |
| 2007/0291491 A1* | 12/2007 | Li et al. | 362/307 |
| 2008/0073616 A1 | 3/2008 | Dong et al. | |
| 2008/0112153 A1 | 5/2008 | Iwasaki et al. | |
| 2008/0123339 A1* | 5/2008 | Bierhuizen et al. | 362/293 |
| 2008/0290362 A1* | 11/2008 | Zhang et al. | 257/99 |
| 2008/0291682 A1 | 11/2008 | Falicoff et al. | |
| 2009/0040598 A1 | 2/2009 | Ito | |
| 2009/0052158 A1* | 2/2009 | Bierhuizen et al. | 362/84 |
| 2009/0154137 A1 | 6/2009 | Bierhuizen et al. | |
| 2009/0168395 A1* | 7/2009 | Mrakovich et al. | 362/84 |
| 2009/0207480 A1* | 8/2009 | Onishi et al. | 359/326 |
| 2009/0219586 A1 | 9/2009 | Fujimoto et al. | |
| 2011/0037948 A1 | 2/2011 | Horvath et al. | |
| 2011/0149246 A1 | 6/2011 | Artsyukhovich | |
| 2011/0149591 A1 | 6/2011 | Smith | |

OTHER PUBLICATIONS

Written Opinion of the International Searching Authority, International Application No. PCT/US2011/027,936, May 4, 2011, 5 pages.

International Search Report for PCT/US2010/059264, 2 pages.

Written Opinion of the International Searching Authority, International Application No. PCT/US2010/059264, (Mar. 1, 2011), 5 pages.

International Search Report for PCT/US2012/052200 dated Oct. 26, 2012, 2 pages.

International Search Report for PCT/US2010/059264 dated Mar. 1, 2011, 2 pages.

* cited by examiner

APPARATUS FOR ENHANCING BRIGHTNESS OF A WAVELENGTH CONVERTING ELEMENT

BACKGROUND

Anatomically, an eye may be divided into two distinct parts—an anterior segment and a posterior segment. The anterior segment includes a lens and extends from an outermost layer of the cornea (the corneal endothelium) to a posterior of a lens capsule. The posterior segment includes a portion of the eye behind the lens capsule. The posterior segment extends from an anterior hyaloid face (part of a vitreous body) to a retina, with which the posterior hyaloid face is in direct contact. The posterior segment is much larger than the anterior segment.

The posterior segment includes the vitreous body—a clear, colorless, gel-like substance. It makes up approximately two-thirds of the eye's volume, giving it form and shape before birth. The vitreous body is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free flowing like the aqueous humor and has normal anatomic attachment sites. One of these sites is the vitreous base, which is an approximately 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to the aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions, such as a fiber optic light source, to illuminate inside the eye; an infusion line to maintain the eye's shape during surgery; and instruments to cut and remove the vitreous body.

During such surgical procedures, proper illumination of the inside of the eye is important. Typically, a thin optical fiber is inserted into the eye to provide the illumination. A light source, such as a halogen tungsten lamp or high pressure arc lamp (metal-halides, Xe), may be used to produce the light carried by the optical fiber into the eye. The light passes through several optical elements (typically lenses, mirrors, and attenuators) and is transmitted to the optical fiber that carries the light into the eye. The advantage of arc lamps is a small emitting area (<1 mm), a color temperature close to daylight, and typically a longer life than halogen lamps (i.e., 400 hours vs. 50 hours). The disadvantage of arc lamps is high cost, decline in power over time, complexity of the systems and the need to exchange lamps several times over the life of the system.

In an effort to overcome some of the limitations of halogen tungsten lamps and high pressure arc lamps, other light sources, such as light emitting diodes (LEDs), may be used to produce the light transmitted through the optical fiber into the eye. LED based illuminators may be provided at considerably lower cost and complexity, and may exhibit characteristic life times of 50,000 to 100,000 hours, which may enable operating an ophthalmic fiber illuminator for the entire life of the instrument with very little drop in output and without the need to replace LEDs. LED light sources, however, generally exhibit lower luminous efficiency and decreased luminous flux than comparable halogen tungsten lamps and high pressure arc lamps.

DETAILED DESCRIPTION

Figure 1:
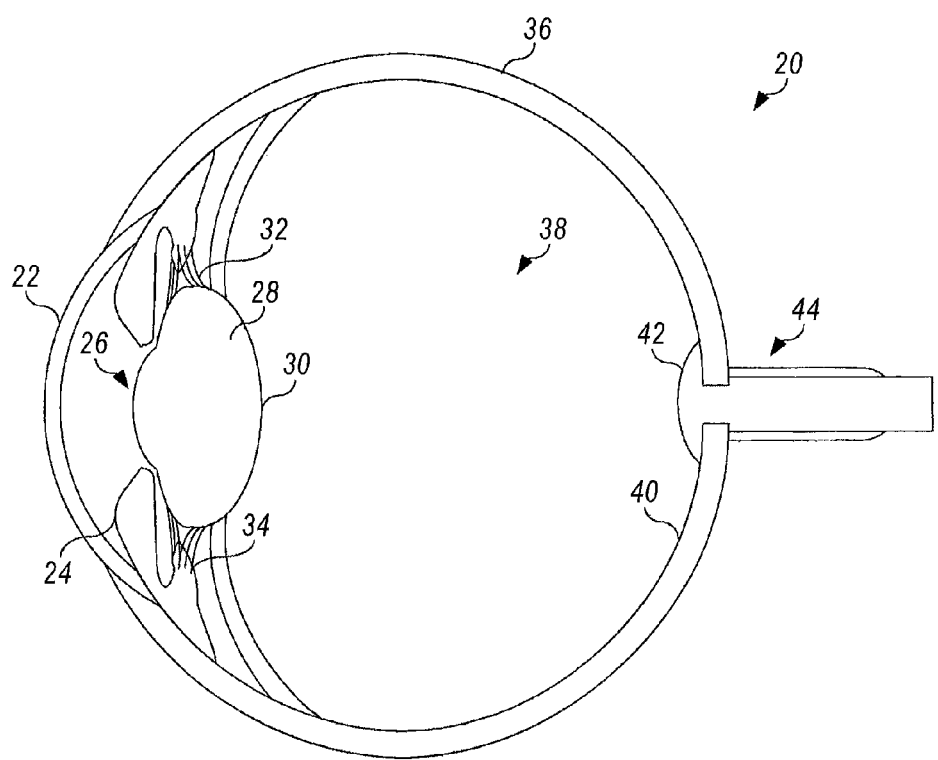
FIG. 1 is a cross-sectional view of an eye illustrating an internal anatomy of the eye.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive, otherwise limit, or restrict the claims to the precise forms and configurations shown in the drawings and disclosed in the following detailed description.

FIG. 1 illustrates an anatomy of an eye 20, which includes a cornea 22, an iris 24, a pupil 26, a lens 28, a lens capsule 30, zonules 32, ciliary body 34, sclera 36, vitreous region 38, retina 40, macula 42, and optic nerve 44. Cornea 22 is a clear, dome shaped structure on the surface of eye 20 that acts as a window, letting light into the eye. Iris 24, which corresponds to the colored part of the eye, is a muscle surrounding pupil 26 that relaxes and contracts to control the amount of light entering eye 20. Pupil 26 is a round, central opening in iris 24. Lens 28 is a structure inside eye 20 that helps focus light on retina 40. Lens capsule 30 is an elastic bag that encapsulates lens 30, helping to control the shape of lens 28 as the eye focuses on objects at different distances. Zonules 32 are slender ligaments that attach lens capsule 30 to the inside of eye 20, holding lens 28 in place. Ciliary body 34 is a muscular area attached to lens 28 that contracts and relaxes to control the size of the lens for focusing. Sclera 36 is a tough, outermost layer of eye 20 that maintains the shape of the eye. Vitreous region 38 is a large, gel-filled section located towards a back of eye 20 that helps maintain the curvature of the eye. Retina 40 is a light-sensitive nerve layer at the back of eye 20 that receives light and converts it into signals to send to the brain. Macula 42 is an area in the back of eye 20 that includes receptors for detecting fine detail in a viewed image. Optic nerve 44 transmits signals from eye 20 to the brain.

Figure 2:
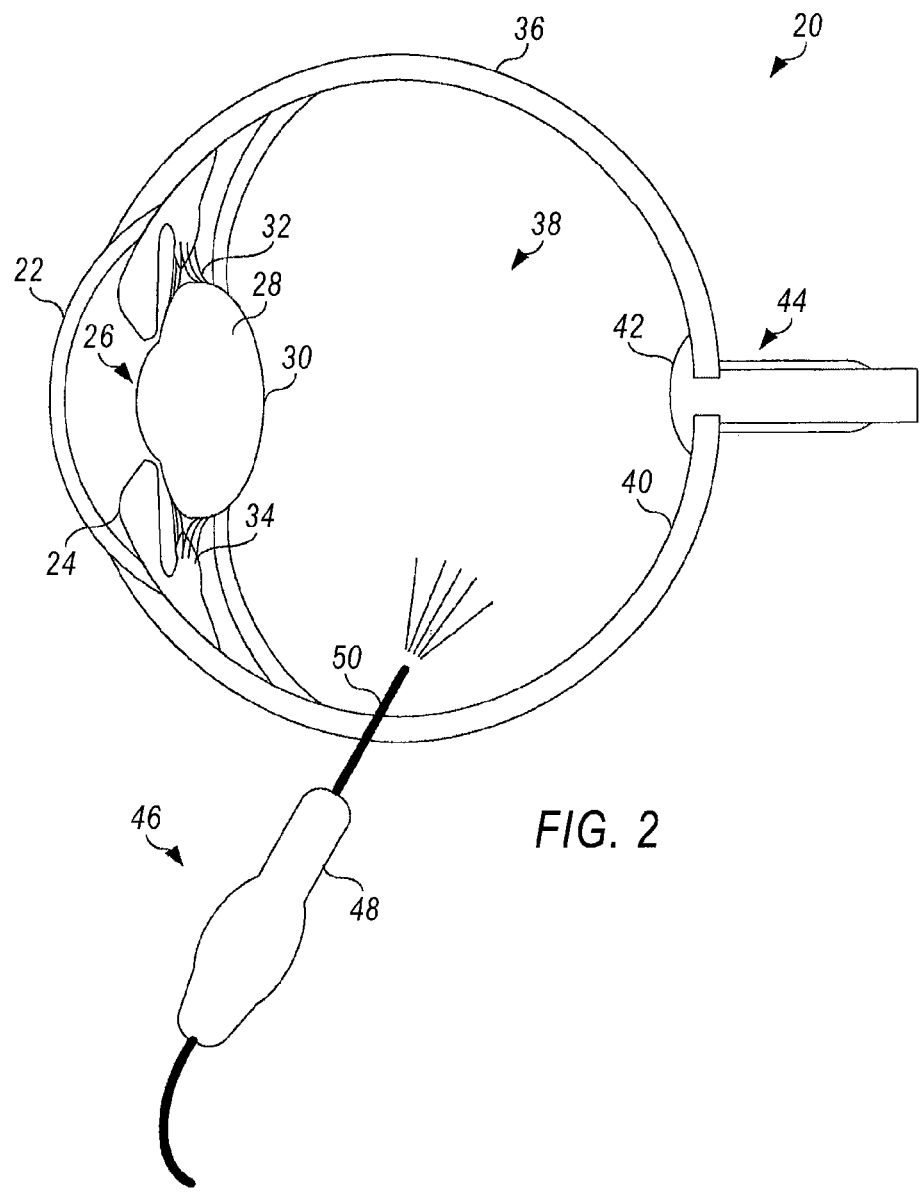
FIG. 2 is schematic illustration of an exemplary endoilluminator shown illuminating an interior region of the eye of FIG. 1.

With reference to FIG. 2, an ophthalmic endoilluminator 46 for illuminating an interior of eye 20 is shown inserted through sclera 36 into vitreous region 38. Endoilluminator 46 may include a handpiece 48 and a probe 50. Probe 50 may be inserted into eye 20 through an incision in the sclera 36. Probe 50 may include a fiber optic wire for transferring light from a light source to illuminate the inside of vitreous region 38 of eye 20 during various intra-optical procedures, such as vitreo-retinal surgery. Endoilluminator 46 may employ various light sources, such as a halogen tungsten lamp, a high-pressure arc lamp (metal-halides, Xe), and a light emitting diode (LED). A light pump may be employed with endoilluminator 46, particularly when using an LED light source, to help enhance the brightness of the light. Various configurations of a light pump that may be employed with endoilluminator 46 are illustrated in FIGS. 3-9.

Figure 3:
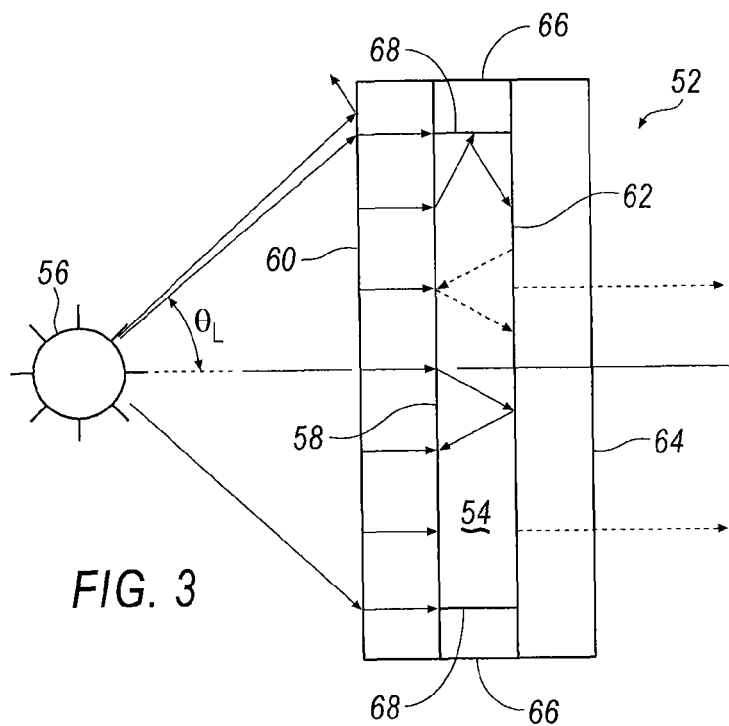
FIG. 3 is a schematic partial cross-sectional view of an exemplary light pump that may be employed with the endoilluminator of FIG. 2.

Referring to FIG. 3, a light pump 52 may include a wavelength converting element (WCE) 54 that receives light from a light source 56. Wavelength converting element 54 may have a generally planar plate-like configuration, although other shapes may also be employed, for example, to accommodate production constraints or to optimize optical performance. Arranged adjacent a first side 58 of wavelength converting element 54 is a first dichroic element 60, and arranged adjacent a second side 62 of wavelength converting element 54 is a second dichroic element 64. In the illustrated exemplary configuration, dichroic elements 60 and 64 are shown engaging wavelength converting element 54, but one or both of the dichroic elements may be spaced apart from the wavelength converting element. Light pump 52 may also include a reflecting optical element 66 arranged along a side edge 68 of wavelength converting element 54. Reflecting optical element 66 may engage wavelength converting element 54, as shown in FIG. 3, or may be spaced apart from the wavelength converting element 54.

Light source 56 may include one or more monochromatic LEDs configured to emit light within a relatively narrow range of wavelengths, such as ultraviolet (UV), violet, or blue light. The relatively narrow light band produced by light source 56 when using monochromatic LEDs is generally not suitable for illumination. To produce light having a broader range of wavelengths, at least a portion of the light from light source 56 is directed onto wavelength converting element 54, where the light is converted to light having a broader range of wavelengths.

Wavelength converting element 54 may have a variety of configurations. The term "wavelength converting element", as used herein, refers generally to any structure formed from a material capable of converting electromagnetic radiation, in a particular range of the electromagnetic spectrum, to another range within the electromagnetic spectrum, including but not limited to, the down-conversion of high-energy photons (e.g., particle rays, x-rays, UV, and low-wavelength visible light) to lower energy photons or the up-conversion of low energy photons (e.g., infrared, near-infrared, or visible red) to high energy photons. Any suitable type of wavelength converting element for producing illumination may be employed. The luminescence process utilized for conversion may be based on either slow emission (phosphorescence) or fast emission (fluorescence), depending on the type of materials used in wavelength converting element 54.

For convenience, light having a wavelength within the range produced by light source 56 shall hereinafter be referred to as "unconverted light," whereas light having a wavelength within the range produced by wavelength converting element 54 shall hereinafter be referred to as "converted light." Furthermore, light having a wavelength within the range produced by light source 56 (i.e., unconverted light) is represented throughout the figures by a solid line, and light having a wavelength within the range produced by wavelength converting element 54 (i.e., unconverted light) is represented throughout the figures by a dashed line.

Wavelength converting element 54 may be used, for example, to convert UV/violet/blue light illumination from light source 56 into broadband or white light through luminescence or phosphorescence. The luminescence/phosphorence generally occurs in all directions (i.e., isotropically), rather than along a particular light beam path (i.e., directionally). Further, not all of the unconverted light from light source 56 that reaches wavelength converting element 54 is converted to the desired wavelength range. Rather, a portion of the light may be reflected back toward light source 56, or may pass entirely through wavelength converting element 54. Both of these phenomena operate to reduce the operating efficiency of light pump 52. The operating efficiency of light pump 52 may be improved through use of dichroic elements 60 and 64, and reflective optical element 66.

To help improve the conversion efficiency of wavelength converting element 54, first dichroic element 60 may be configured to allow unconverted light from light source 56 to pass through first dichroic element 60 to wavelength converting element 54, and to reflect converted light back onto wavelength converting element 54. Second dichroic element 64 may be configured to allow converted light to pass through dichroic element 64, and to reflect unconverted light back onto wavelength converting element 54. Further, reflective optical element 66 may be configured as a broadband reflector to reflect both converted and unconverted light back onto wavelength converting element 54. Dichroic elements 60 and 64, and reflective optical element 66, together operate to help prevent unconverted light from escaping wavelength converting element 54, which may thereby increase the conversion efficiency of wavelength converting element 54. First dichroic element 60 and reflective optical element 66 also operate together to help direct converted light out the front of wavelength converting element 54 (i.e., away from light source 56) by minimizing the amount of converted light emitted from side edge 68 and first side 58 (i.e., toward light source 56) of wavelength converting element 54.

Figure 4:
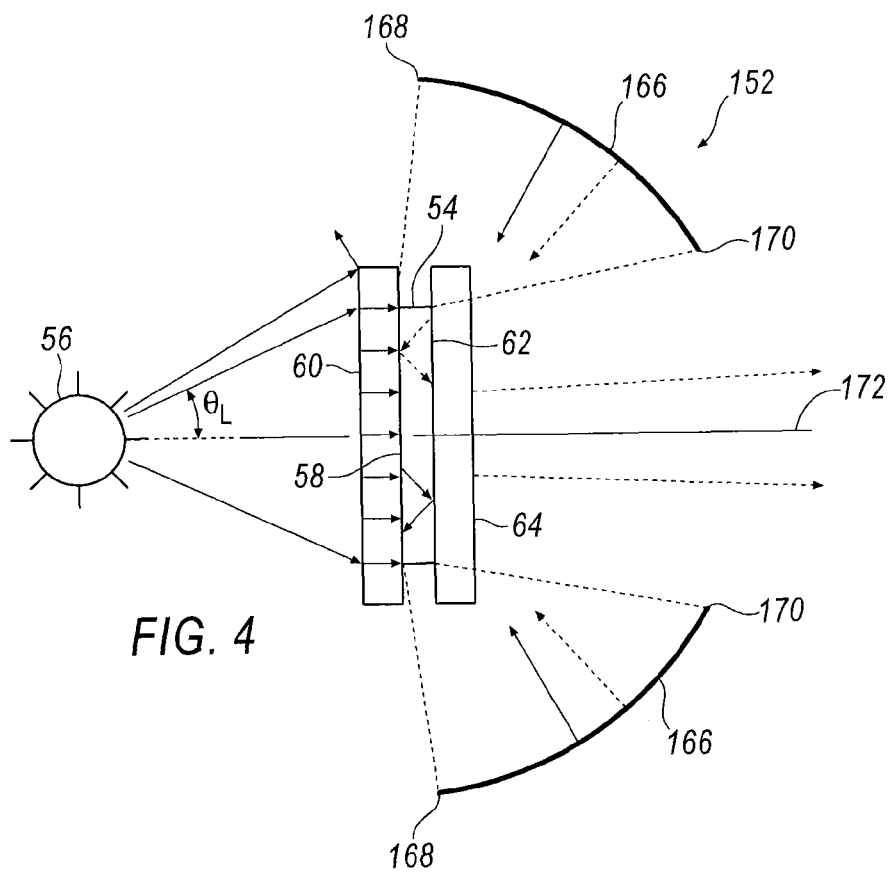
FIG. 4 is a schematic partial cross-sectional view of an exemplary light pump employing a reflective optical element and a pair of dichroic elements arranged on opposite sides of a wavelength converting element.

With reference to FIG. 4, an alternately configured light pump 152 is illustrated. Light pump 152 may include features to better control the size and direction of a beam of converted light emitted from light pump 152. Light pump 152 may be similarly configured as light pump 52, shown in FIG. 3, with the exception that a reflective optical element 166 may be substituted in place of reflective optical element 66 (FIG. 3). Reflective optical element 166 may be configured as a broadband reflector to reflect both converted and unconverted light back onto wavelength converting element 54. Light pump 152 also includes wavelength converting element 54 and dichroic elements 60 and 64, each of which are configured and operate in the same general manner as describe previously with respect to light pump 52 (FIG. 3).

Reflective optical element 166 may have a generally concave shape relative to wavelength converting element 54. Reflective optical element 166 includes a proximal end 168 and an opposite distal end 170. Proximal end 168 may be arranged axially along an optical axis 172 of light pump 152 in a general vicinity of a wavelength converting element 54 or beyond it. Distal end 170 may be arranged along optical axis 172 at a distance from wavelength converting element 54 that is greater than a distance between proximal end 168 and wavelength converting element 54. Due to the curvature of reflective optical element 166, a distance between proximal end 168 and optical axis 172 is greater than a distance between distal end 170 and optical axis 172. Second dichroic element 64 may be positioned along optical axis 172 between proximal end 168 and distal end 170 of reflective optical element 166.

Figure 5:
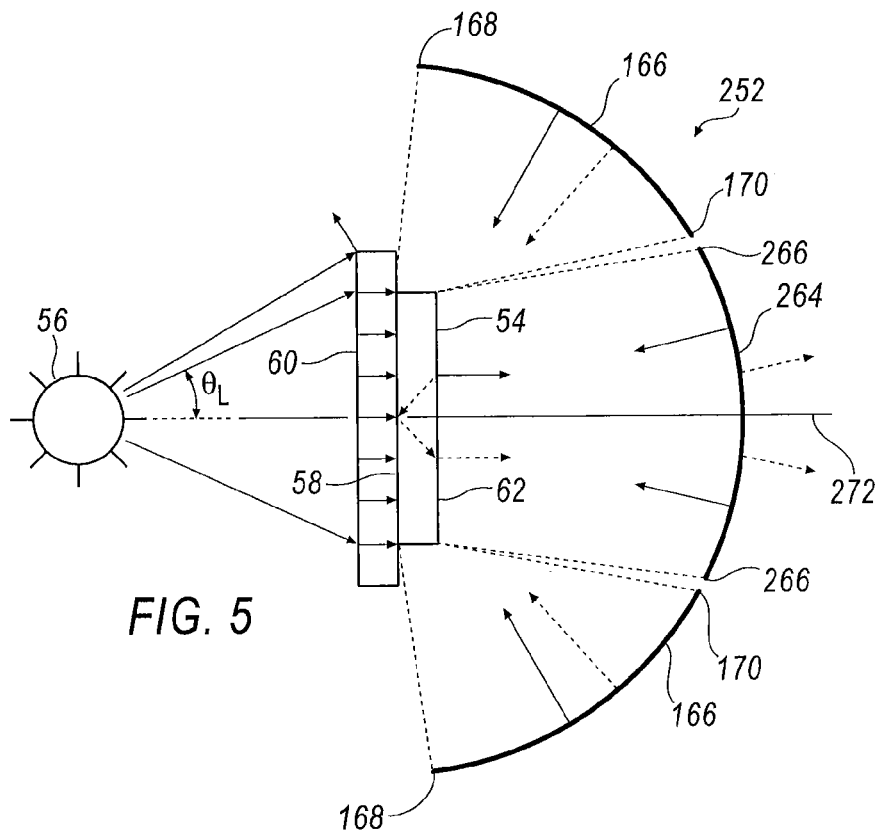
FIG. 5 is a schematic partial cross-sectional view of the exemplary light pump of FIG. 4, with one of the dichroic elements displaced away from the wavelength converting element.

With reference to FIG. 5, an alternately configured light pump 252 is illustrated. Light pump 252 may be similarly configured as light pump 152, shown in FIG. 4, with the exception that a second dichroic element 264 may be substituted in place of second dichroic element 64 (FIG. 4). Second dichroic element 264 may be configured to allow converted light to pass through dichroic element 264, and to reflect unconverted light back onto wavelength converting element 54. Light pump 252 also includes wavelength converting element 54, first dichroic element 60 (FIG. 4), and reflective optical element 166 (FIG. 4), each of which is configured and operates in the same general manner as described previously with respect to light pump 152 (FIG. 4).

Second dichroic element 264 may have a generally concave shape relative to wavelength converting element 54. Second dichroic element 264 is generally displaced away from wave converting element 54, such that no portion of the dichroic element contacts wavelength converting element 54. In the exemplary configuration illustrated in FIG. 5, substantially the entire second dichroic element 264 is positioned at a further distance from wavelength converting element 54 than distal end 170 of reflective optical element 166. Second dichroic element 264 may also be positioned at other locations along an optical axis 272 relative to distal end 170 of reflective optical element 166, which may include positions that are closer or further away from wavelength converting element 54. For example, all or a portion of second dichroic element 264 may be positioned along optical axis 272 between wavelength converting element 54 and distal end 170 of reflective optical element 166. Second dichroic element 264 may be sized so as to not overlap reflective optical element 166, as shown in FIG. 5, or may be sized to overlap reflective optical element 166, in which case an end 266 of second dichroic element 264 would be at a further distance from optical axis 272 than distal end 170 of reflective optical element 166.

Figure 6:
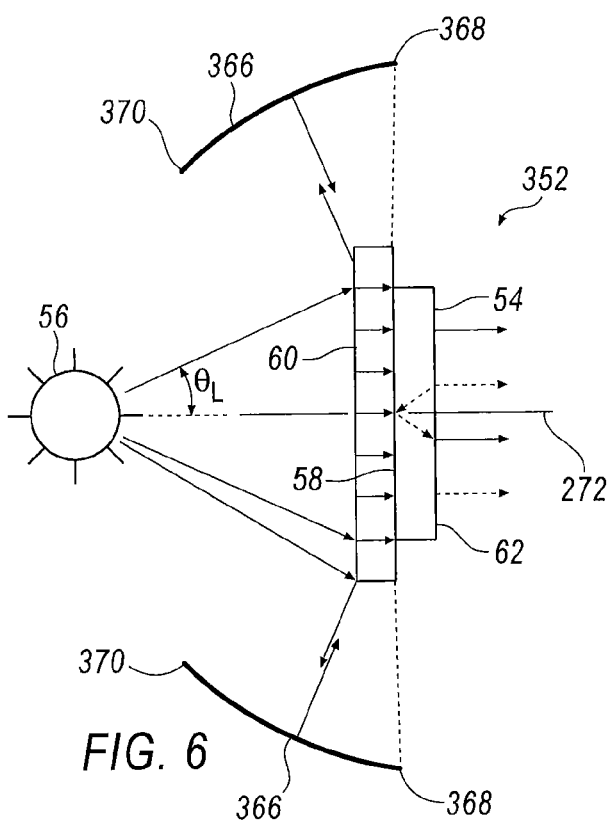
FIG. 6 is a schematic partial cross-sectional view of an exemplary light pump employing a reflective optical element and a dichroic element arranged adjacent a wavelength converting element.

With reference to FIG. 6, an alternately configured light pump 352 is illustrated. Light pump 352 may include features to better control an incidence angle at which light from light source 56 arrives at first dichroic element 60, and to increase the amount of unconverted light that reaches wavelength converting element 54. Light pump 352 may be similarly configured as light pump 52, shown in FIG. 3, with the exception that a reflective optical element 366 may be substituted in place of reflective optical element 66 (FIG. 3). Light pump 352 may also include wavelength converting element 54 and first dichroic element 60, each of which is configured and operates in the same general manner as describe previously with respect to light pump 52 (FIG. 3). Although not shown in FIG. 6, light pump 352 may also include second dichroic element 64, which is configured and operates in the same general manner as described previously.

Dichroic optical elements, such as first dichroic element 60, typically have a limited range of incidence angles at which light arriving at the dichroic element will be allowed to pass through the optical element. Light arriving at an incidence angle outside the permissible range will generally be reflected from the dichroic element. For example, in FIG. 6, unconverted light from light source 56 arriving at first dichroic element 60 with an incidence angle less than $\theta_L$ will pass through first dichroic element 60 to wavelength converting element 54. Unconverted light arriving at an incidence angle greater than $\theta_L$ will reflect off first dichroic element 60 and not reach wavelength converting element 54. Reflective optical element 366, may be used to redirect the reflected unconverted light back to dichroic element 60. Reflective optical element 366 may be configured to reflect only the unconverted light, or may be configured as a broadband reflector to reflect both converted and unconverted light back onto first dichroic element 60.

Reflective optical element 366 may have a generally concave shape relative to wavelength converting element 54. Reflective optical element 366 includes a proximal end 368 and an opposite distal end 370. Proximal end 368 may be arranged axially along an optical axis 272 of light pump 352 in a general vicinity of a wavelength converting element 54. Distal end 370 may be arranged along optical axis 272 at a distance from wavelength converting element 54 that is greater than a distance from proximal end 368 to wavelength converting element 54. Due to the curvature of reflective optical element 366, a distance from proximal end 368 to optical axis 272 is greater than a distance from distal end 370 to optical axis 272. First dichroic element 64 may be positioned along optical axis 272 between proximal end 368 and distal end 370 of reflective optical element 166.

Figure 7:
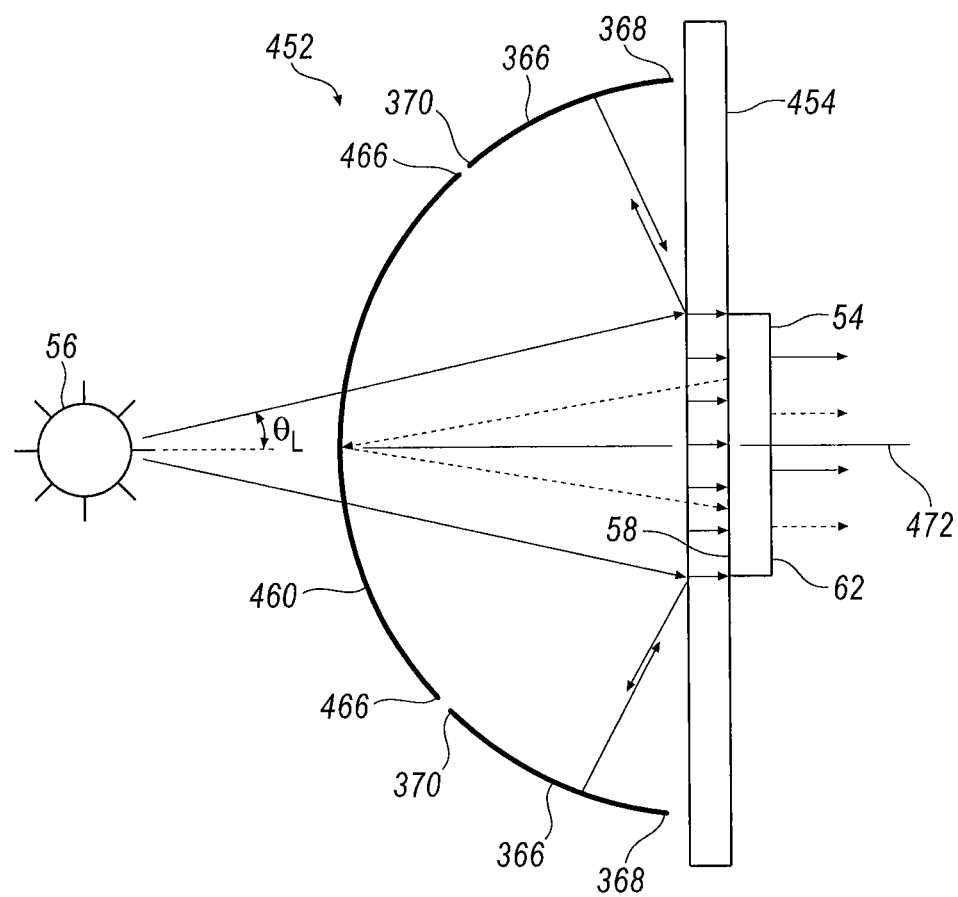
FIG. 7 is a schematic partial cross-sectional view of the exemplary light pump of FIG. 6, with the dichroic element displaced away from the wavelength converting element.

With reference to FIG. 7, an alternately configured light pump 452 is illustrated. Light pump 452 may be similarly configured as light pump 352, shown in FIG. 6, with the exception that a first dichroic element 460 may be substituted in place of first dichroic element 60 (FIG. 6). First dichroic element 460 may be configured to allow unconverted light to pass through dichroic element 460, and to reflect converted light back onto wavelength converting element 54. Light pump 452 also includes wavelength converting element 54 and reflective optical element 366 (FIG. 6), each of which is configured and operates in the same general manner as describe previously with respect to light pump 352 (FIG. 6). Wavelength converting element 54 may be attached to an optically transparent support member 454. Although not shown in FIG. 7, light pump 452 may also include second dichroic element 64, which is generally configured and operates in the same manner as previously described.

First dichroic element 460 may have a generally concave shape relative to wavelength converting element 54. First dichroic element 460 is generally displaced away from wavelength converting element 54, such that no portion of the dichroic element contacts wavelength converting element 54.

In the exemplary configuration illustrated in FIG. 7, substantially the entire first dichroic element 460 is positioned at a further distance from wavelength converting element 54 than distal end 370 of reflective optical element 366. First dichroic element 460 may also be positioned at other locations along an optical axis 472 relative to distal end 370 of reflective optical element 366, which may include positions that are closer or further away from wavelength converting element 54. For example, all or a portion of first dichroic element 460 may be positioned along optical axis 472 between wavelength converting element 54 and distal end 370 of reflective optical element 366. First dichroic element 460 may be sized so as to not overlap reflective optical element 366, as shown in FIG. 7, or may be sized to overlap reflective optical element 366, in which case an end 466 of first dichroic element 460 would be at a further distance from optical axis 472 than distal end 370 of reflective optical element 366.

Figure 8:
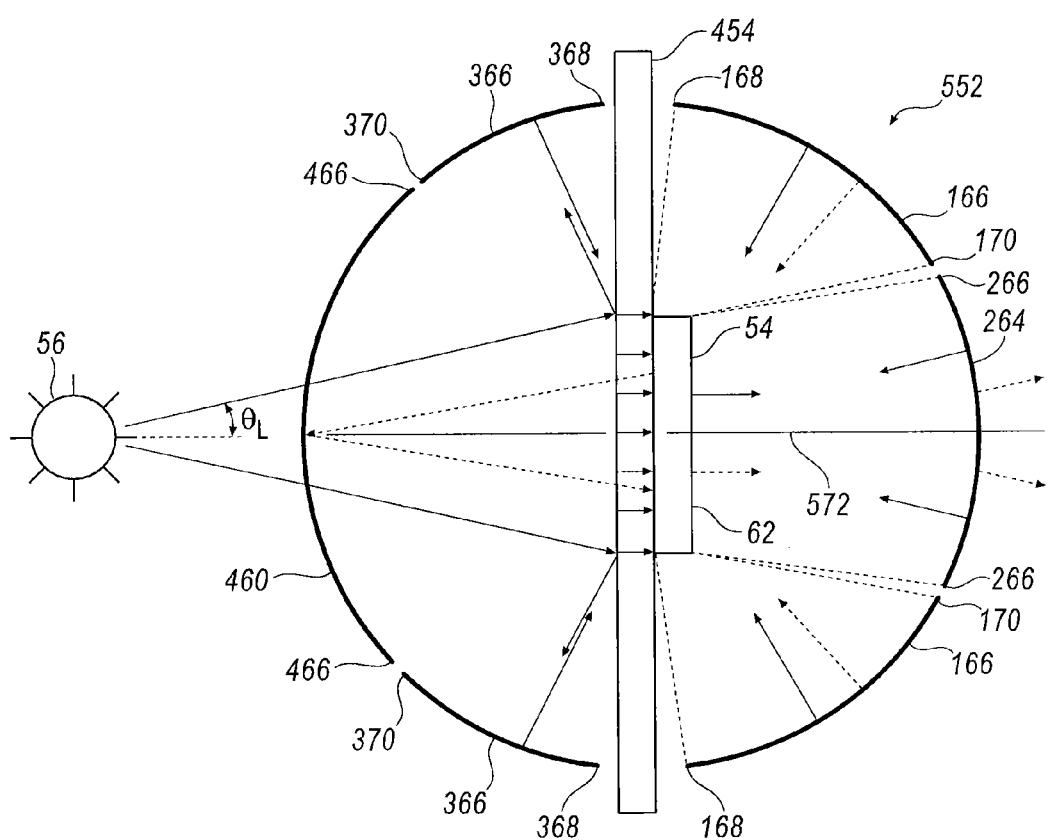
FIG. 8 is a schematic partial cross-sectional view of an exemplary light pump employing the features of the light pump of FIG. 5 and the light pump of FIG. 7.

With reference to FIG. 8, an alternately configured light pump 552 is illustrated. Light pump 552 combines the features of light pump 252 (FIG. 5) and light pump 452 (FIG. 7). Each of the optical elements may be configured and operate as generally described previously with respect to light pump 252 and light pump 452. An optical axis 572 of light pump 552 corresponds to optical axis 272 of light pump 252, and optical axis 472 of light pump 452.

Figure 9:
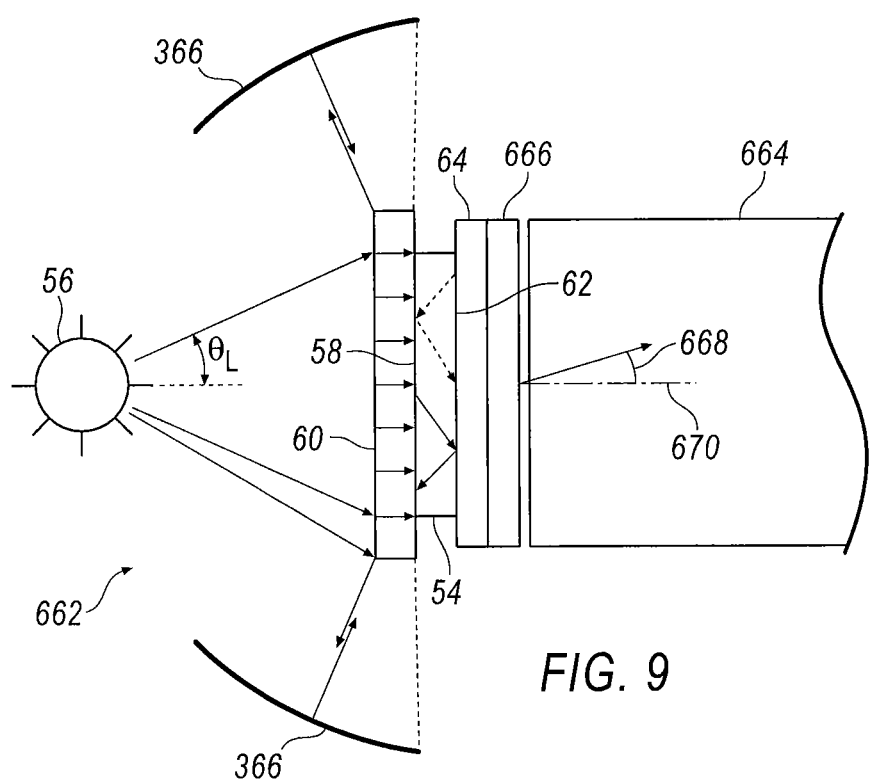
FIG. 9 is a schematic partial cross-sectional view of an exemplary light pump optically coupled to an optical fiber.

Referring to FIG. 9, a mechanism for optically connecting light pump 662 to an optical fiber 664 of endoilluminator 46 is illustrated. Light pump 662 may include a variety of configurations. In one exemplary configuration, light pump 662 is configured similar to light pump 352 (FIG. 6), and may include wavelength converting element 54, first dichroic element 60, second dichroic element 64, and reflective optical element 366, each of which is configured and operates in the same general manner as previously describe.

First dichroic optical element 60 may be configured to pass unconverted light from light source 56, and to reflect converted light back onto wavelength converting element 54. Second dichroic optical element 64 may be configured to pass converted light emitted from wavelength converting element 54, and to reflect unconverted light back onto wavelength converting element 54. Reflective optical element 366, may be used to redirect reflected unconverted light from first dichroic element 60 back to dichroic element 60. Reflective optical element 366 may be configured to reflect only the unconverted light, or may be configured as a broadband reflector to reflect both converted and unconverted light back onto first dichroic element 60.

Light pump 662 may include an angle of incidence sensitive element 666 positioned between second dichroic element 64 and optical fiber 664. Incidence sensitive element 666 may be configured to block passage of converted light exiting second dichroic element 64 at an incidence angle exceeding a predetermined limit. Optical fiber 664 includes a maximum emission angle 668, which is an angle relative to a fiber axis 668 at which light may enter the fiber and travel along its length. A numerical aperture (NA) may be determined for optical fiber 664 based on the fiber's maximum acceptance angle. Incidence sensitive element 666 may be configured to have a numerical aperture that is compatible with the numerical aperture of optical fiber 664, which will help ensure that light exiting incidence sensitive element 666 will be able to enter and travel within optical fiber 664.

It will be appreciated that the exemplary brightness enhancing apparatus described herein has broad applications. The foregoing configurations were chosen and described in order to illustrate principles of the methods and apparatuses as well as some practical applications. The preceding description enables others skilled in the art to utilize methods and apparatuses in various configurations and with various modifications as are suited to the particular use contemplated. In accordance with the provisions of the patent statutes, the principles and modes of operation of the disclosed docking station have been explained and illustrated in exemplary configurations.

It is intended that the scope of the present methods and apparatuses be defined by the following claims. However, it must be understood that the disclosed docking station may be practiced otherwise than is specifically explained and illustrated without departing from its spirit or scope. It should be understood by those skilled in the art that various alternatives to the configuration described herein may be employed in practicing the claims without departing from the spirit and scope as defined in the following claims. The scope of the disclosed docking station should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. An illumination device comprising:
    a wavelength converting element operable for receiving light at a first face from a light source at a first wavelength range and converting the light to a second wavelength range, the wavelength converting element having the first face, a second face opposite the first face, and a side edge extending between the first and second faces;
    a first dichroic element arranged adjacent the first face of the wavelength converting element, the first dichroic element configured to allow passage of light in the first wavelength range into the wavelength converting element and block passage of light in the second wavelength range; and
    a curved reflective optical element arranged adjacent the side edge of the wavelength converting element and between the light source and the wavelength converting element, the reflective optical element configured to reflect light from the first dichroic element in at least the first wavelength range prior to passing through the wavelength converting element back to the wavelength converting element.

2. The illumination device of claim 1, wherein the reflective optical element includes a first region arranged at a first axial point along an optical axis of the illumination device and a second region arranged at a second axial point along the optical axis of the illumination device, a distance along the optical axis from the first axial point to the wavelength converting element being less than a distance along the optical axis from the second axial point to the wavelength converting element, and a distance from the first axial point to the first region of the reflective optical element being greater than a distance from the second axial point to the second region of the reflective optical element.

3. The illumination device of claim 1, wherein the first dichroic element is configured to block passage of light having one of the first wavelength range and the second wavelength range, and to allow passage of light in the remaining wavelength range.

4. The illumination device of claim 1, wherein at least a portion of the first dichroic element engages the wavelength converting element.

5. The illumination device of claim 1, further comprising:
a second dichroic element arranged adjacent the second face of the wavelength converting element, the second dichroic element configured to block passage of light in the first wavelength range and allow passage of light in the second wavelength range; and
wherein the wavelength converting element is arranged between the first and second dichroic elements.

6. The illumination device of claim 5 further comprising an angle of incidence sensitive element arranged adjacent the second dichroic element, the angle of incidence sensitive element configured to allow passage of light approaching the angle of incidence sensitive element at angle less than or equal to a preselected angle of incidence, and to block passage of light approaching at an angle greater than the preselected angle of incidence.

7. The illumination device of claim 1, wherein at least a portion of the reflective optical element engages the wavelength converting element.

8. The illumination device of claim 1, wherein substantially the entire reflective optical element is displaced away from the wavelength converting element.

9. The illumination device of claim 1, wherein the reflective optical element is configured to reflect light in the second wavelength range back toward the wavelength converting element.

10. The illumination device of claim 1, wherein the reflective optical element includes a concave region relative to the wavelength converting element.

11. An illumination device comprising:
a wavelength converting element operable for receiving light from a light source at a first wavelength range and converting the light to a second wavelength range, the wavelength converting element including a first face for receiving the light from the light source, a second face opposite the first face, and a side edge extending between the first and second faces;
a first dichroic element arranged adjacent the first face of the wavelength converting element;
a second dichroic element arranged adjacent the second face of the wavelength converting element; and
a curved reflective optical element arranged adjacent the side edge of the wavelength converting element and between the light source and the wavelength converting element, the reflective optical element configured to reflect at least one of light from the first dichroic element in the first wavelength range prior to passing through the wavelength converting element and light in the second wavelength range to the wavelength converting element.

12. The illumination device of claim 11, wherein the first dichroic element is configured to pass light in the first wavelength range and to reflect light in the second wavelength range.

13. The illumination device of claim 12, wherein the first dichroic element is arranged between the light source and the wavelength converting element.

14. The illumination device of claim 11, wherein the second dichroic element is configured to pass light in the second wavelength range and to reflect light in the first wavelength range.

15. The illumination device of claim 14, wherein the wavelength converting element is arranged between the light source and the second dichroic element.

16. The illumination device of claim 11, wherein one of the first dichroic element and the second dichroic element engage the wavelength converting element, and the remaining dichroic element is disposed away from the wavelength converting element.

17. The illumination device of claim 11, wherein the first and second dichroic elements both engage the wavelength converting element.

18. The illumination device of claim 11, wherein the first and second dichroic elements are both disposed away from the wavelength converting element.

19. The illumination device of claim 11, wherein the reflective optical element includes a concave region relative to the wavelength converting element.

20. The illumination device of claim 11, wherein the reflective optical element engages at least one of the first and second dichroic elements.

21. The illumination device of claim 11, wherein substantially the entire reflective optical element is displaced away from the wavelength converting element.

* * * * *